United States Patent [19]

Young et al.

[11] Patent Number: 5,429,814
[45] Date of Patent: * Jul. 4, 1995

[54] MOLECULAR SIEVE-ENCLOSED TRANSITION AND RARE EARTH METAL IONS AS CONTRAST AGENTS FOR THE GASTROINTESTINAL TRACT

[75] Inventors: Stuart W. Young, Portola Valley, Calif.; Kenneth J. Balkus, Jr., The Colony; A. Dean Sherry, Dallas, both of Tex.

[73] Assignee: Board of Regents, The University of Texas System, Austin, Tex.

[*] Notice: The portion of the term of this patent subsequent to Jun. 16, 2009 has been disclaimed.

[21] Appl. No.: 70,351

[22] PCT Filed: Dec. 6, 1991

[86] PCT No.: PCT/US91/09222
§ 371 Date: May 27, 1993
§ 102(e) Date: May 27, 1993

[87] PCT Pub. No.: WO92/10213
PCT Pub. Date: Jun. 25, 1992

Related U.S. Application Data

[63] Continuation-in-part of Ser. No. 624,106, Dec. 7, 1990, Pat. No. 5,122,363.

[51] Int. Cl.$^6$ ............................................. A61B 5/055
[52] U.S. Cl. .................................. 424/9.31; 436/173; 436/9.32; 424/684; 514/836; 514/974; 423/328.1
[58] Field of Search ............... 424/9, 4, 684; 436/173; 128/653.4, 654; 514/836, 974; 423/328

[56] References Cited

U.S. PATENT DOCUMENTS

| 4,259,306 | 3/1981 | Pelrine | 423/325 |
| 4,388,285 | 6/1983 | Rankel et al. | 423/329 |
| 4,466,812 | 8/1984 | Takaishi et al. | 55/68 |
| 4,500,503 | 2/1985 | Rankel et al. | 423/329 |
| 4,647,447 | 3/1987 | Gries et al. | 424/9 |
| 4,767,609 | 8/1988 | Stavrianpoulous | 424/1.1 |
| 4,774,957 | 10/1988 | Nambu et al. | 128/653 |
| 4,797,267 | 1/1989 | Kuehl | 423/329 |
| 4,943,545 | 7/1990 | Chang et al. | 502/56 |
| 5,122,363 | 6/1992 | Balkus, Jr. et al. | 424/9 |

FOREIGN PATENT DOCUMENTS 0186616 7/1986 European Pat. Off.
8911874 12/1989 WIPO.

OTHER PUBLICATIONS

Article in German by Claussen et al., "Orale Kontrastmittel für die magnetische Resonanztomographie des Abdomens. Teil III: Erste Patientenuntersuchungen mit Gadolinium-DTPA", RöFo, vol. 148, pp. 683–689, 1989.

Article by Braybrook and Hall, "Effect of pH on the Nuclear Magnetic Resonance Relaxivity of Encapsulated Solid Paramagnetic Substances", Drug Design and Delivery, vol. 4, pp. 93–95, 1989.

Article by Denkewicz, "Zeolite Science: An Overview", Journal of Materials Education, vol. 9, No. 5, pp. 519–564, 1987.

(List continued on next page.)

Primary Examiner—Gary E. Hollinden
Attorney, Agent, or Firm—Arnold, White & Durkee

[57] ABSTRACT

The invention relates to a method of using molecular sieve-enclosed paramagnetic ions as image brightening or image contrast agents. In particular, zeolite enclosed trivalent gadolinium is useful in MRI studies of the entire gastrointestinal tract, providing excellent images. Zeolite-enclosed gadolinium complexes may be conveniently administered in oral preparations without side effects of diarrhea. Other transition metal ions, including divalent manganese may be enclosed in any suitable molecular sieve which has ion exchange properties sufficient to exchange the selected metal. The exchanged paramagnetic metal ion may be a free ion within the zeolite framework or ligated with a chelator. Alternatively, a paramagnetic metal ion may be included as part of the molecular sieve framework.

25 Claims, 3 Drawing Sheets

OTHER PUBLICATIONS

Article by Hahn et al., "First Clinical Trial of a New Superparamagnetic Iron Oxide for Use As an Oral Gastrointestinal Contrast Agent in MR Imaging", Radiology, vol. 175, pp. 695–700, 1990.

The Condensed Chemical Dictionary, Van Nostrand Reinhold Company, publishers, Eighth Edition, p. 190, 1971.

Atlas of Zeolite Structures, Butterworths, publisher, Second Revised Edition, 1987, p. 344.

Ismatov et al., "Solid Solutions with the Composition $Ca_7TRAl_{17}S=i_{15}O_{64}$ with the Anorthite Structure," *Chemical Abstracts, Abstract No. 114935j, 103:676, 1985.*

Nemoshkalenko et al., "Electronic Structure of Intermetallic Compounds of $RAl_2Si$ Type," *Chemical Abstracts*, Abstract No. 27525g, 103:327, 1985.

Nesper et al., "Gadolinium Aluminum Silicide ($GdAl_2Si_2$), an Unexpected Compound of the Calcium Aluminum Silicide ($Ff_2Si_2$) Type," *Chemical Abstracts*, Abstract No. 82704t, 98:658, 1983.

Brown et al., Medical Physics 11(1):67–72 (1984).

MOLECULAR SIEVE-ENCLOSED TRANSITION AND RARE EARTH METAL IONS AS CONTRAST AGENTS FOR THE GASTROINTESTINAL TRACT

This is a 371 of PCT/US91/09222 filed Dec. 6, 1991, which is a continuation-in-part of U.S. Pat. No. 5,122,363 issued Jun. 16, 1992, the entire disclosure of which is herewith incorporated by reference and without disclaimer.

The invention relates to contrast or imaging agents useful in vivo for studies and diagnosis of the gastrointestinal tract. The agents are molecular sieve materials enclosing a paramagnetic ion such as trivalent gadolinium. The loaded molecular sieves are particularly suitable for oral administration and function well as magnetic resonance imaging contrast or image brightening agents in the upper gastrointestinal tract.

The availability of sophisticated methods such as MRI and CT has contributed to the increased use of imaging technology in therapy and diagnostic studies. Gastrointestinal tract imaging is a particular area of interest because currently used imaging agents generally provide poor imaging, resulting in visualization of little more than gross blockages or anatomical abnormalities.

Barium sulfate and paramagnetic iron oxide are agents traditionally used for gastrointestinal studies. The latter material has become popular because of the paramagnetic properties of $Fe_2O_3$ which is suited for MRI studies, but it has many disadvantages. These include black bowel, side effects of diarrhea and, from an important analytical standpoint, the presence of artifacts arising from clumping. When paramagnetic iron concentrates, it may become ferromagnetic, drastically altering its imaging properties. Even when images are obtained, the signal is black, making it difficult to distinguish imaged from nonimaged areas.

The development of imaging contrast agents, particularly for gastrointestinal tract studies has been slow. Historically, the most popular agent has been superparamagnetic iron oxide for magnetic imaging, due to its nonbiodegradability. Although good contrast effects have been achieved in some MR studies in the small bowel, increasing occurrence of blurring and "metal" artifacts in the distal part of the bowel has been recorded (Lonnemark et al., 1989). In other studies with superparamagnetic iron oxide, good resolution of the head and tail of the pancreas, anterior margins of the kidneys and para-aortic region has been shown in human patients. However, there are undesirable side effects such as episodes of diarrhea in some patients (Hahn et al., 1990).

Magnetic imaging is particularly useful for the study and diagnosis of tumors or inflammatory abdominal diseases. Paramagnetic species represented by gadolinium seem to be potentially agents for these studies, the metal itself cannot be used in humans because of its toxic properties. Nevertheless, diethylenetriamine penta-acetic acid (DTPA) complexes of trivalent gadolinium have less toxicity than the uncomplexed salt and have been tested in human patients. Opacification of the gastrointestinal tract has been reported, but less than 60% of the magnetic resonance scans showed improved delineation of abdominal pathologies. Furthermore, nearly 40% of the patients reported diarrhea and meteorism (Claussen et al., 1989).

Encapsulation of solid paramagnetic complexes in sulfonated ion-exchange resins for use in abdominal imaging has been suggested. It has been speculated that such encapsulation in acid-stable materials would prevent significant demetallation which otherwise occurs in the stomach when image contrasting agents are orally administered for gastrointestinal tract imaging (Braybrook and Hall, 1989).

Superparamagnetic iron oxide has been coated onto a polymer carrier matrix and evaluated as an oral contrast medium for MRI. Generally good images were obtained in the region of the small bowel, except the duodenum, but the useful concentration range appeared to be fairly narrow since some concentrations caused an artifact in the stomach after ingestion of the agent (Lonnemark et al., 1989).

There is clearly a need for orally effective, well-tolerated agents that can be used in humans for imaging studies. In particular, an MRI imaging agent applicable to gastrointestinal tract studies would be useful for visualizing the anatomy of the intestinal tract and particularly to differentiate normal and pathological states, such as tumors. An effective, orally deliverable paramagnetic imaging contrast agent devoid of the common side effects currently encountered with the presently used GI imaging agents would represent a significant improvement over the iron and gadolinium complexes described. These compounds have several problems, including toxicity and lack of good image quality. Even with reports of improved compositions such as carrier complexes and matrices, some areas of the intestine are inadequately visualized with these materials and side effects still exist. For example, although trivalent gadolinium is an excellent paramagnetic MRI contrast species, its toxicity limits use in humans to its DTPA complex, which itself may exhibit toxicity.

The present invention addresses one or more of the foregoing or other problems associated with use of presently available agents of choice in imaging studies, particularly in gastrointestinal imaging. A nontoxic zeolite molecular sieve carrier that preferentially binds paramagnetic metal ions within a lattice-like structure has been shown to have little toxicity and to exhibit excellent imaging properties. Furthermore, many of the problems associated with the use of superparamagnetic iron oxide are eliminated, including metal imaging and patient side effects such as diarrhea.

In one aspect of the invention, a zeolite-enclosed paramagnetic metal ion is utilized for contrast imaging in animals or humans. Effective, sharp imaging is possible because the paramagnetic ion remains relatively tightly held within the zeolite matrix, being preferentially bound compared with cations such as sodium.

Preparations of paramagnetic metal ions enclosed in a zeolite molecular sieve are orally administrable and, because little leakage of potentially harmful metal ions occurs, nontoxic. Preferred paramagnetic species include trivalent gadolinium and divalent manganese with trivalent gadolinium enclosed in a faujasite group zeolite such as CaA or NaX to form CaGdA or NaGdX representing a most preferred embodiment.

Generally, the invention is an imaging method which involves administering a paramagnetic ion enclosed in zeolite. Most often the method will be used in humans but of course it could be used in animals, for example, in veterinary practice for diagnosis of gastrointestinal abnormalities. The amount of paramagnetic ion enclosed within the zeolite is enough to be effective as a contrast or imaging brightening agent. A particularly useful feature of this invention is the brightness of the areas imaged with zeolite enclosed paramagnetic ions. This contrasts with images obtained with superparamagnetic iron oxide which develop as dark or deep gray areas. Brightly imaged areas are preferred over dark contrast for visualizing the anatomy of the area and for detecting pathologies because delineation is increased.

Zeolite-enclosed paramagnetic ions are particularly useful for imaging studies in human beings and have many advantages over superparamagnetic iron oxide. Superparamagnetic iron tends to clump in the gastrointestinal tract causing a conversion from paramagnetic to ferromagnetic properties. Additionally, superparamagnetic iron oxide administered in the quantities necessary for satisfactory imaging causes unpleasant side effects in human beings, including diarrhea and meteorism. Such effects have not been observed with zeolite-enclosed trivalent gadolinium. The invention also overcomes the problems associated with toxicity of some of the paramagnetic metals considered most useful for MRI studies, for example trivalent gadolinium. Toxicity of trivalent gadolinium has been reduced by combining it with dimethyltetraaminopentaacetic acid (DTPA) to form a complex that exhibits less toxicity than the gadolinium salt. However, some studies with gadolinium DTPA indicate problems similar to those encountered with super paramagnetic iron oxide, such as side effects of diarrhea and meteorism. In addition, the toxicity of the complex has not been fully determined. On the other hand, toxicity has not been observed with the use of zeolite-enclosed gadolinium. This may be due to relatively tight binding of the metal ion within the zeolite molecular sieve.

Although the invention has been illustrated with trivalent gadolinium and divalent manganese, other ion species that ion exchange with a zeolite may be used. Examples include tetravalent vanadium, trivalent vanadium, divalent copper, divalent nickel, trivalent chromium, divalent cobalt, divalent iron, trivalent iron and trivalent cobalt. Any of a number of salts of these species may be used to exchange a resident counterion in the zeolite, including chlorides, acetates, nitrates and the like. These examples are not intended to be limiting; for example, other species capable of ion exchanging include members of the lanthanide series of elements and the rare earth elements.

There are numerous zeolites capable of entrapping paramagnetic ions and are therefore suitable for the practice of the invention. For example, the synthetic zeolites type A, type X, type Y or ZSM-5 type zeolite are particularly useful (Breck, 1984; Rankel and Valyocsik, 1983). Type X and type Y zeolites are faujasite (FAU) group zeolites, while type A zeolites are Linde type A zeolites (LTA). Many types of molecular sieves are available, differing in chemical composition, cavity diameter or natural occurrence, such as the mordenite class of zeolites. Shapes of these substances are to some extent derived from the linkages of secondary building units forming the typical three-dimensional framework of the molecules. The shapes may then have an effect on ion exchange ability, selectivity in restricting the passage of molecules based on size, and absorption properties.

Many molecular sieves that would not be considered zeolites also may be used to enclose metal ions useful for imaging. Zeolites are a particular class of molecular sieves having an aluminosilicate framework structure. Zeolite building blocks are $Si^{+4}$ and $Al^{+4}$ tetrahedra linked through common oxygen atoms extending in an infinite 3-dimensional network. When isomorphic atoms are substituted for aluminum or silicon (e.g., gallium, germanium or phosphorus), synthetic molecular sieves are created. Framework atoms may also be substituted with paramagnetic ions such as $Mn^{2+}$ or $Gd^{3+}$. Molecular sieves, especially those that possess ion exchange properties, may be used analogously to zeolites.

Ion exchange properties of the zeolite are especially important in preferential binding of certain ions, particularly metal ions of the transition metal series. The amount of metal ion actually enclosed within the zeolite will depend on the characteristics of the particular zeolite type used, as well as the presence of other positively charged ions. Thus, for example, if calcium zeolite type A is mixed with a gadolinium salt and allowed to equilibrate over a period of time, the final exchange product will contain both positively charged gadolinium and calcium ions. However, these zeolites will preferentially exchange with the transition metal ions giving rise to greater concentrations of the transition metal ions than the ions from group 1 or group 2 elements when both types of ions are present. At any rate, the preferential binding of paramagnetic ions such as $Gd^{+3}$ and $Mn^{+2}$ is sufficient to give excellent MRI imaging properties when the zeolite-entrapped paramagnetic ion is used for imaging studies.

In another embodiment of the invention, complexed paramagnetic ions are enclosed within a zeolite matrix. Intrazeolite complexes may be prepared by at least two different methods, either by synthesizing the zeolite around a complex or by diffusing a ligand into the zeolite where it then complexes with the metal ion. Typical complexing agents include 8-hydroxyquinoline, dipiconilic acid and phthalic acid, but numerous other ligands may also be employed and may depend on the particular paramagnetic ion chosen for complexation. One consideration in the selection of a ligand is the number of occupied sites on the metal ion. While 4–6 bonds will generally more tightly bind a metal ion, it may in some circumstances be desirable to employ fewer bonds, 2 for example, so that bulk water is more available to the metal. Increased access to bulk water, as a general principle, enhances imaging intensities. Improved imaging may then be achieved with lower amounts of paramagnetic material.

A second consideration in the selection of a ligand is binding affinity. A larger number of ligands, e.g., 4–6, may be desirable to provide tighter binding to preclude loss of potentially toxic free metal ions. Multidentate ligands generally form more stable complexes and are preferred. The ligands may be neutral or carry a charge where the complex would preferably have available a positive charge. Additionally, the ligand may have a paramagnetic functional group such as a nitroxide. The ligand radical combined with the metal ion may further enhance imaging intensities.

Yet another embodiment of the invention is a paramagnetic metal ion enclosed in a molecular sieve both as a free metal ion, for example ion-exchanged into the molecular sieve, and as a complexed metal ion. Such a composition has the advantage of the relatively high loading of a paramagnetic ion exchanged zeolite, combined with the advantages of having a paramagnetic ion held in the larger cavities of the zeolite, being therefore more accessible to bulk water and enhancing image intensity. Complexation, especially chelation, localizes the active species in larger pores with better access to water, yet reduces loss of the ion from the zeolite matrix. This may become a consideration if, for example, the zeolite were to partially digest after administration for diagnostic purposes.

Zeolite enclosed paramagnetic ions are particularly useful for MRI studies of the gastrointestinal tract, especially since pharmaceutically acceptable preparations of these materials can be administered enterically, for example, by nasogastric tube to either an animal or a human being. Oral administration is preferred for most applications involving studies or treatment of humans.

Detection of a molecular sieve enclosed paramagnetic ion after administration is most preferably performed by magnetic resonance imaging, although conventional radiographic imaging and computerized tomography (CT) may also be employed in a manner similar to techniques used with $BaSO_4$ and gastrographin imaging. High Z (atomic weight) metals like gadolinium may also be detected by monochromatic x-ray sources, for example, K-edge imaging. Additionally, certain zeolite-enclosed metal complexes may be detected by fluorescence.

In a most preferred method of practice, the invention is used for gastrointestinal tract imaging. A pharmaceutically acceptable formulation including zeolite enclosed trivalent gadolinium is administered, preferably orally, to a human or animal and detected by magnetic resonance imaging. The trivalent gadolinium may be enclosed within calcium type A zeolite, sodium type X zeolite or other suitable molecular sieve. In preferred practice, zeolite enclosed trivalent gadolinium is prepared in a pharmaceutical carrier prior to administration.

The zeolite enclosed metal ion compounds of this invention may be combined with pharmaceutically acceptable formulating agents, dispersing agents and fillers. Powders, granules, capsules, coated tablets, syrupy preparations and aqueous suspensions may be utilized for oral preparations. Formulating agents employed may be either solid or liquid, including but not limited to such solids as calcium phosphate, calcium carbonate, dextrose, sucrose, dextrin, sucrose ester, starch, sorbitol, mannitol, crystalline cellulose, talc, kaolin, synthetic aluminum silicate, carboxymethyl cellulose, methylcellulose, cellulose acetate phthalate, alginates, polyvinyl pyrrolidone, polyvinyl alcohol, gum arabic, tragacanth gum, gelatin, bentonite, agar powder, shellac, Tween 80, carrageenans and psyllium. Modified zeolite materials having residual charges or modifying groups might also be used which may be adsorbed to various carrier matrices such as clay. Examples of liquids suitable as suspending fluids include water, isotonic salt solution, ethanol, propylene glycol, polyethylene glycol, glycerol, Hartman's solution and Ringer's solution. A preferred liquid for suspension is EZpaque supernatant which is readily obtained from EZpaque after removing $BaSO_4$, either by centrifugation or filtration.

Administration is most preferably oral because of better patient acceptance in that form but administration may also be intravascular, enteric, vaginal, anal or by direct introduction into the gastrointestinal tract at any point such as by introduction through tubes accessing the alimentary canal. Flavor enhancers may be added to oral preparations, including taste masking substances such as sweeteners and citrus flavors. Other additives, including color, preservatives, bulk or antifoam agents may also be included in the formulation.

Examples of non-oral use include retrograde pelvic studies and investigations to define vaginal contents. Intravascular administration is also expected to be effective. Particulates such as colloidal iron oxide have been injected into the bloodstream without ill effect, indicating that stable molecular sieve particulates would likewise cause no problems as carriers.

The invention may also be used in conjunction with magnetic resonance imaging of body surfaces. For example, artificial limbs must be custom fitted to leg, arm, hand or foot amputees. Present methods are time-consuming and rendered difficult because photographs show only skin surface while x-ray indicates only dense material such as bone. MRI could show both bone and skin and therefore facilitate design of a prosthetic device which must be customized to the remaining member of the body. Zeolite-enclosed trivalent gadolinium would be ideal for this purpose. The crystalline material would be powdered sufficiently to be conveniently applied to a skin surface, preferably as an aerosol which could be either a dry powder or a suspension in a suitable fluid, for example water or alcohol. The skin is preferably first treated with an agent that promotes adherence of the powder to the surface, for example, tincture of benzoin. Other applications envisioned are imaging of the foot, useful in customizing footwear for abnormal or injured feet. Surface imaging could also be used in connection with inanimate surfaces, for example some metal surfaces. In some cases, especially where high resolution is desired, uniform application would be important so that surface roughness reflected the surface examined rather than an artifact of uneven application.

Zeolites having appropriate crystal dimensions may also be used as intravascular MRI contrast agents. While oral preparations may be preferred by patients, direct injection into the bloodstream may provide advantages such as speed or visualization of constricted areas.

The zeolite enclosed ionic species of this invention will typically be formulated as suspensions or dispersions, preferably in EZ dispersant (available from E-ZM Company) or used as the supernatant from pharmacy-purchased suspensions of $BaSO_4$ under the trade name of EZpaque) at a low weight to volume ratio. For oral administration this is preferably approximately 1%. Higher concentrations of the zeolite composition may be prepared as suspensions; however, for MR imaging purposes, image intensity decreases markedly above weight ratios of 1%. The 1% suspensions in EZpaque supernatant appear to be stable indefinitely.

A marked advantage of calcium gadolinium enclosed in type A zeolite is the relatively low concentration that may be employed in a dispersing medium. For example, a one percent concentration of calcium gadolinium type A zeolite administered orally is effective in producing excellent images for MRI studies, although higher weight percent concentrations may be utilized in accordance with the form of the preparation. In contrast, when barium sulfate is used in the same dispersing medium, concentrations of up to 40-50% by weight are required and precipitation is often a problem.

A most preferred paramagnetic ion useful for GI studies of this sort is trivalent gadolinium, however, other metal ions as listed above can be used. Excellent results have also been obtained using zeolite enclosed divalent manganese.

It will be appreciated by those of skill in the art that there will always be present within the zeolite not only the paramagnetic ion, complexed or free, which is used for the imaging, but also a second ion with which the paramagnetic ion was exchanged. The type of second ion will depend on the zeolite compound used in the preparation. For example, calcium zeolite, calcium type A zeolite, sodium zeolite or other salts formed from first and second group elements may be used. Alternatively, the parent zeolite could be exchanged with protons, alkali or alkaline earth metal ions, transition or rare earth metal ions prior or subsequent to entrapment of a paramagnetic ion. It should be further understood that a molecular sieve enclosing a paramagnetic ion may contain other ligands such as hydroxyl ion, chloride ion or water depending on the method of preparation. Any or all of these species may affect the properties of the enclosed ions. The presence of any one or a number of these may alter or attenuate the pharmacological effects of the zeolite enclosed paramagnetic ion.

BRIEF DESCRIPTION OF THE DRAWING

FIGS. 1A–1B is an MRI scan of the gastrointestinal tract of a rabbit taken after two administrations by NG tube of a 1% suspension of CaGdA at 12 hr and 4 hr before MRI scanning.

FIGS. 2A and 2B are scans taken 1 hr after administration.

The present invention relates particularly to pharmaceutical compositions that include zeolite-enclosed paramagnetic ions and the utility of these species as contrast and image brightening agents. Suitable paramagnetic ions may be enclosed in a wide range of zeolites, either as a "free" ion within the zeolite cage or complexed with an appropriate complexing agent. By free ion is meant a charged species lacking ligands, but not necessarily precluding charge-charge interactions with other species. Such interactions may be in the form of counterion interactions within the cages of the enclosing zeolite, or, as compounds forming the zeolite framework, for example replacement of the metal portion of the aluminate.

Methods of preparation of zeolite enclosed metal ions are well-known in the art, and are generally based on the ion exchange properties of zeolites. Thus a paramagnetic ion such as gadolinium may be exchanged into many types of zeolites, including most of the faujasite group of zeolites, or even molecular sieves with ion-exchange properties.

In addition to zeolite-enclosed "free" metal ions, it has been discovered that useful imaging compositions may be obtained from zeolite-enclosed metal ion chelate complexes. Examples are provided showing that metal ion chelates may be formed in situ, that is, after the ion is enclosed within the zeolite, or, metal ion complexes may be enclosed by synthesizing the zeolite around a metal ion chelate.

Sodium type A and type X zeolites readily form around gadolinium(III) complexes of 8-hydroxyquinoline, dipiconilic acid and phthalic acid. Other suitable ligands may include salicylamide, salicylic acid, anthranilic acid, bipyridine, terpyridine, phenanthroline, ethylenediamine, bis(salicylaldehyde)ethylenediamine, ethylenediamine diacetic acid or the like. Chelated paramagnetic species, as a general rule, are larger than the free ion and therefore must be located in the larger spaces within the zeolite structure. Consequently, the paramagnetic ion is more accessible to water than ions located in smaller spaces. At comparable loadings of paramagnetic ion, intensities are higher for chelated ions compared with free ion counterparts within the zeolite.

Intensities measured with zeolite-enclosed chelated paramagnetic ions indicate that complexation causes localization of the active metal in larger pores with better access to water; however, this does not preclude use of both chelated and ion exchanged metal ions. The intrazeolite papramagnetic complexes, as disclosed herein, may be prepared by at least two different methods, either by synthesizing the zeolite around a complex or by diffusing the ligand into the zeolite to form a complex. Chelation is also expected to function as a second line of defense against any toxicity, as in instances where a zeolite might be partially digested.

Not all molecular sieves exhibit ion exchange properties, but several species do have this property, including aluminosilicates, silicoaluminum phosphates and metalloaluminum phosphates. Complexed paramagnetic ions as herein disclosed are expected to be useful in successfully encapsulating a paramagnetic species, and thus expanding the range of zeolite-type compounds able to enclose metal ions with little or no loss of the paramagnetic material.

In certain applications, such as blood pool agents, stability and stability may not be major concerns. In such instances, chelates with a minimal number of ligands may be desirable in order to provide a maximal number of sites for water coordination. In general, the more accessible the paramagnetic ion is to bulk water, the more intense a signal measured. Where stability is important, multidentate ligands with a larger number of binding sites may be desired to assure retention of a toxic metal ion.

The following examples illustrate preferred embodiments of the practice of the invention. It should be understood that these examples are intended to be illustrative of the invention and in no way limiting.

EXAMPLE 1

Preparation of Zeolite-Enclosed Trivalent Gadolinium

Calcium zeolite (calcium A), 10 g, was mixed with 2 g of $GdCl_3 \cdot 6H_2O$ in approximately 100 ml deionized water and stirred at 30° C. for 18 hr. The resulting zeolite suspension was suction filtered and washed extensively with deionized water until negative for chloride ion by silver nitrate test. The resulting CaGdA gave a negative test for free $Gd^{+3}$ using the colorimetric indicator, xylenol orange. The zeolite was dried in a vacuum oven overnight at 50° C. The resulting sample contained 3.24% trivalent gadolinium by weight. Analogous procedures using NaA, NaX or NaY yielded the percent weight compositions shown in Table 1. $MnCl_2$ used in place of $GdCl_3$ formed MnNaX when exchanged into NaX.

TABLE 1

| Compound | Weight percent metal |
| --- | --- |
| GdNaA | 6.18 |
| GdCaA | 3.24 |
| GdNaX | 6.19 |

TABLE 1-continued

| Compound | Weight percent metal |
|---|---|
| GdNaY | 3.11 |
| MnNaX | 5.59 |

The various zeolites shown in Table 1 were suspended in EZ dispersant at the indicated weight percent. Image intensity data were recorded as shown in Table 2.

TABLE 2

| Compound | Intensity[1] | Std. Deviation | % sol'n* |
|---|---|---|---|
| GdNaY | 1061.43 | 29.76 | 1 |
| | 382.19 | 12.42 | 0.1 |
| | 259.49 | 8.45 | 0.01 |
| | 228.97 | 8.55 | 0.001 |
| | 187.65 | 7.67 | 0.0001 |
| GdNaX | 454.08 | 19.91 | 1 |
| | 1273.13 | 36.84 | 0.1 |
| | 349.54 | 13.93 | 0.01 |
| | 219.17 | 10.84 | 0.001 |
| | 64.49 | 10.77 | 0.0001 |
| GdNaA | 365.06 | 12.51 | 1 |
| | 1522.71 | 29.67 | 0.1 |
| | 391.05 | 8.90 | 0.01 |
| | 237.03 | 9.37 | 0.001 |
| | 193.79 | 8.39 | 0.0001 |
| GdCaA | 408.25 | 47.06 | 1 |
| | 772.24 | 27.09 | 0.1 |
| | 280.11 | 10.38 | 0.01 |
| | 230.06 | 7.69 | 0.001 |
| | 200.32 | 8.56 | 0.0001 |
| MnNaX | 34.57 | 6.50 | 1 |
| | 1312.48 | 29.02 | 0.1 |
| | 453.10 | 16.17 | 0.01 |
| | 257.36 | 6.90 | 0.001 |
| | 185.37 | 8.66 | 0.0001 |

[1]Mean value
*All sample zeolites suspended in EZpaque supernatant at the indicated wt %.

EXAMPLE 2

Zeolite-Enclosed Complexes of Trivalent Gadolinium Bis(8-hydroxyquinoline)chloro gadolinium(III)

13.5 g of aluminum isopropoxide was mixed with 4.8 g of sodium hydroxide and heated to 90° C. for 0.5 hr before adding 18 ml of water with continued stirring. A silicate solution was prepared by combining 6 g silica, 4.8 g of NaOH and 18 ml of water in a teflon beaker. After the mixture had cooled to room temperature, the silicate and aluminate solutions were combined, followed by the addition of 50 ml of water. 0.18 g of bis(8-hydroxyquinoline)chlorogadolinium(III) was stirred into the gel over a period of 3 hr. The mixture was then heated at 90° C. for 16 hrs in a sealed polypropylene bottle. After cooling to room temperature, the crystals were collected and washed with copious amounts of water. The zeolite crystals were then extracted with toluene for 24 hrs in a Soxhlet extractor to remove surface species. The crystals were suction filtered and dried at 100° C. The sample contained 0.5% gadolinium by weight.

Table 3 shows metal ion loading for the various zeolite-enclosed chelated trivalent gadolinium compositions, the imaging intensity and the weight percent solutions used for the measurements. The values are compared with water, air and the dispersant, EZpaque.

TABLE 3

| | SUMMARY OF ZEOLITE PHANTOMS | | | | | | | | |
|---|---|---|---|---|---|---|---|---|---|
| | % Gd 0.5 X-Gd-7[1] Mean SD | 0.41 X-Gd-8[2] Mean SD | 0.31 X-Gd-9[3] Mean SD | 0.29 A-Gd-5[1] Mean SD | 0.38 A-Gd-6[2] Mean SD | 0.40 A-Gd-7[3] Mean SD | Air Mean SD | Water Mean SD | EZ-PAQUE Mean SD |
| 1% | 416.1 24.8 | 629.9 36.4 | 470.7 37.2 | 257.3 25.9 | 229.5 13.1 | 293.8 11.0 | 4.26 1.5 | 131.8 5.4 | 165.4 6.1 |
| 0.1% | 204.3 7.2 | 318.7 15.8 | 208.0 10.7 | 199.7 9.5 | 212.0 13.8 | 221.3 20.2 | | | |
| 0.01% | 171.8 6.5 | 176.5 7.9 | 163.3 5.6 | 169.5 6.3 | 164.5 7.0 | 172.1 6.1 | | | |
| 0.001% | 163.6 4.9 | 159.7 5.6 | 156.5 7.0 | 158.1 5.9 | 163.8 7.9 | 167.5 6.5 | | | |
| 0.0001% | 159.9 6.2 | 152.3 5.9 | 149. 6.8 | 150.1 7.5 | 157.6 6.7 | 162.0 8.1 | | | |

[1]8-hydroxyquinoline
[2]DPA
[3]phthalic acid

EXAMPLE 3

In Situ Formation of Zeolite-enclosed Trivalent Gadolinium Complexes Sodium X-type Zeolite Complexes NaX zeolite was ion exchanged with $GdCl_3$ followed by exhaustive washing with water, overnight calcination at 350° C. and reaction with 8-hydroxyquinoline. 2.0 g of $Gd^{3+}$-exchanged NaX was slurried for 24 hrs in 100 ml of ethanol containing 1.0 g of 8-hydroxyquinoline. The zeolite was filtered, washed with ethanol and extracted with toluene to remove surface complexes. The sample contained 2.77% Gd by weight.

MFI Type Molecular Sieve containing Trivalent Gadolinium 2 g of silica was dissolved in 3.5 ml of 48% by weight hydrofluoric acid in a teflon beaker. 3 ml water containing 0.19 g of NaOH was added and the mixture allowed to cool to room temperature. 0.2 g of gadolinium trichloride was added (Si/Gd=61) followed by 1.46 g of tetrapropylammonium bromide, 14.3 ml of ammonium hydroxide and an additional 25 ml of water. The gel was aged for 4 hrs, then autoclaved at 150° C. for 24 hrs. After cooling to room temperature, the molecular sieve crystals were washed with water and dried at 90° C.

Table 4 shows the intensity of several different weight percents of gadolinium in type X zeolites after treatment of gadolinium (III) exchanged zeolite with 8-hydroxyquinoline.

TABLE 4

| Compound | Intensity[1] | Standard Deviation | %[2] |
|---|---|---|---|
| 8HQGdX[3] | 954.98 | 36.4 | 1 |
| | 1,380.36 | 50.0 | 0.1 |
| | 431.68 | 17.1 | 0.01 |

TABLE 4-continued

| Compound | Intensity[1] | Standard Deviation | %[2] |
|---|---|---|---|
| | 239.29 | 10.0 | 0.001 |
| EZpaque | 206.59 | 9.6 | |
| Water | 186.51 | 7.1 | |
| Air | 7.78 | 4.2 | |

[1]Mean value
[2]Samples suspended in EZpaque at indicated wt %
[3]$Gd^{+3}$ enclosed in type X zeolite treated with 8-hydroxyquinoline. $Gd^{3+}$ is 3% by weight.

EXAMPLE 4

Figure 1A:
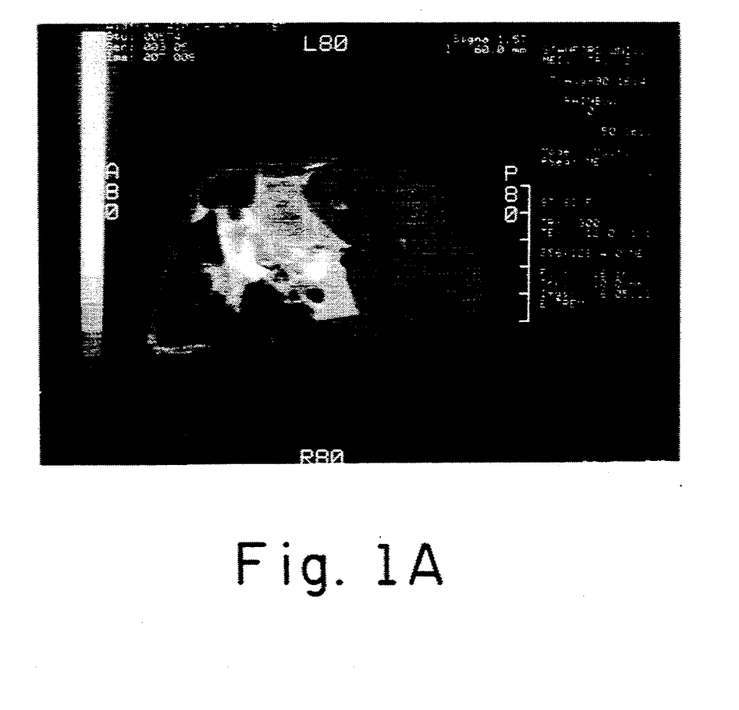
FIG. 1A illustrates the effect of the presence of CaGdA in the stomach.
Figure 1B:
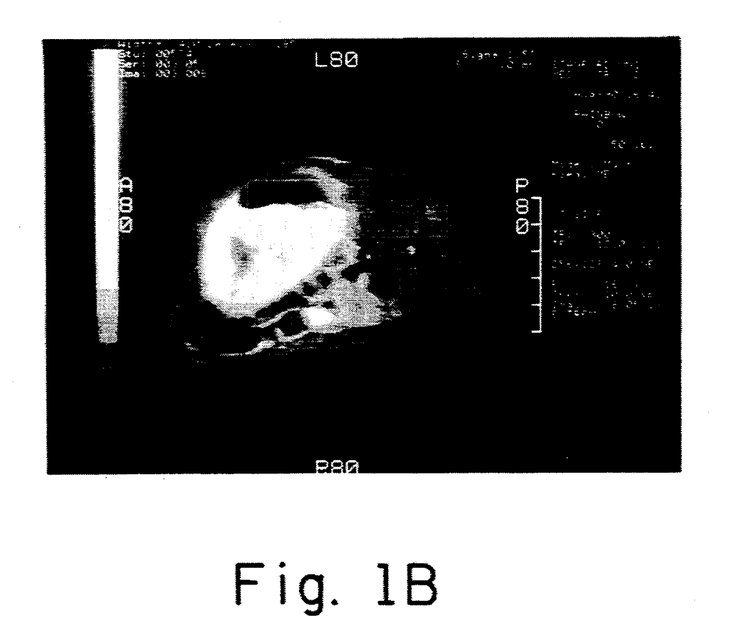
FIG. 1B indicates delineation of the jejunum region of the intestine in the presence of CaGdA.

1 g of CaGdA was suspended in 99 ml dispersing medium prepared from E-Zpaque ™ supernatant obtained by centrifugation of the $BaSO_4$. Approximately 200–300 cc was introduced into the stomach of a rabbit using a pediatric nasogastric (NG) tube at 12 hr and 4 hr prior to MRI. MRI scans were obtained periodically using a conventional $T_1$ weighed sequence. FIG. 1 is an MRI scan 4 hr after the last administration. CaGdA was detected in the stomach, as indicated by the bright region in Panel A. 12 hr after administration the majority of the CaGdA had passed into the intestine and, as shown in Panel B, was concentrated in the jejunum region.

EXAMPLE 5

Gastrointestinal Imaging in the Dog

Figure 2A:
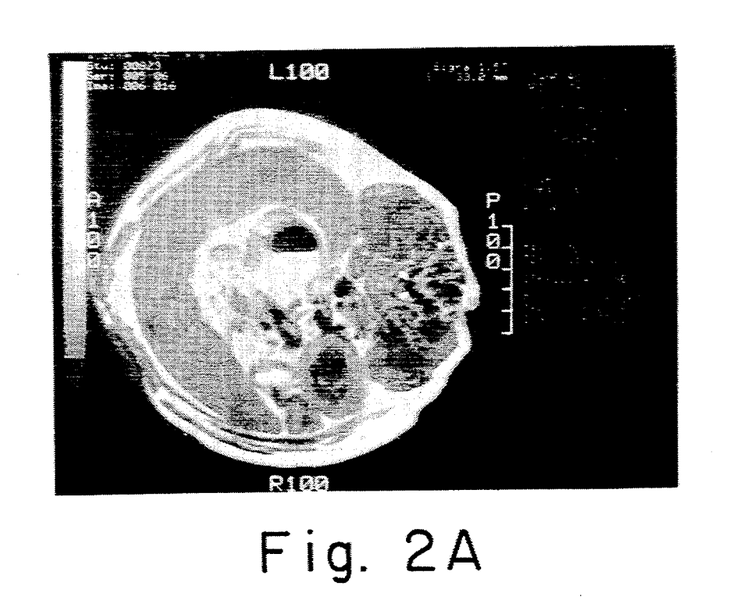
FIGS. 2A–2B is an MRI scan of the gastrointestinal tract of a dog taken after administration by NG tube of a 1% suspension of CaGdA.
Figure 2B:
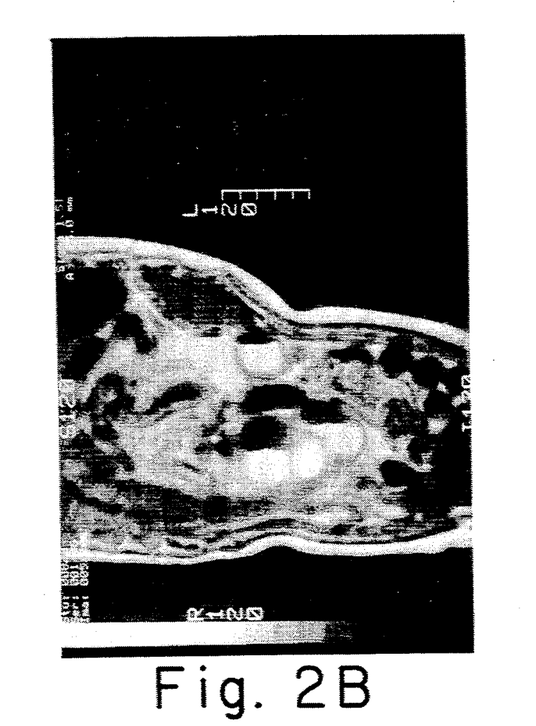
Figure 2C:
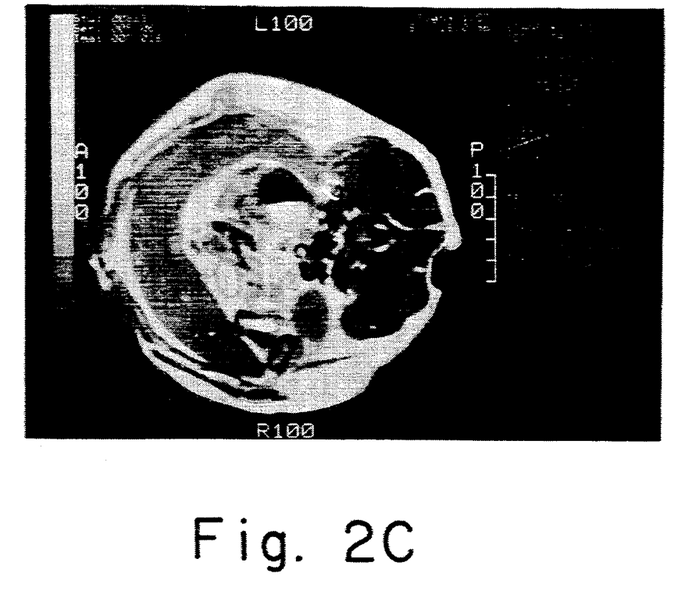
FIGS. 2C and 2D are scans taken 3 hr after administration.
Figure 2D:
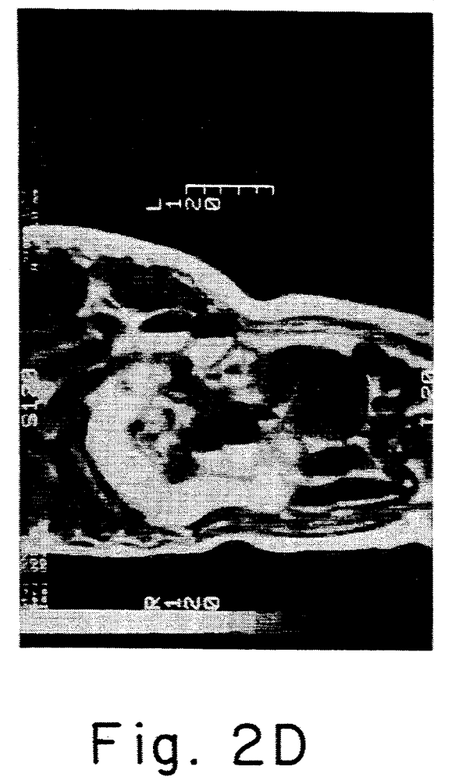

Experimental protocol as described in Example 2 was followed in imaging the gastrointestinal tract of a dog, except that approximately 500 cc of 1% suspension of CaGdA was administered via NG tube. FIG. 2A is an MRI scan taken 1 hour after administration. FIG. 2B is an MRI scan taken 3 hours after administration.

PROPHETIC EXAMPLE 6

The present example outlines the procedure contemplated by the Applicants to be useful for the successful imaging of fistulas.

MRI Fistulagrams

A human patient will have been diagnosed as having a fistula. Generally, indications of infection should not be present as injection of fluid into the fistula might cause delocalization of an infection. In appropriate cases, the fistula will be injected with a suspension of 1% GdNaX in a suitable vehicle such as EZpaque supernatant. 5–15 cc injections will be used, depending on the size of the fistula. Imaging will then be performed using standard MRI procedures in order to visualize extent and location of fistulous tracts.

PROPHETIC EXAMPLE 7

The present example outlines the procedure contemplated by the Applicants to be useful for the successful imaging of the gastrointestinal tract in pediatric practice.

MRI Imaging in Pediatric Patients

Young patients generally do not tolerate hyperosmolic iodinated agents currently in use. The following procedure would be used in this group of patients. The patient is administered 100–150 cc of a 1% solution of GdNaX in EZpaque supernatant or other suitable vehicle via a pediatric NG tube. The administered suspension must not be hyperosmolar. Images are obtained immediately after administration using standard MRI imaging procedures.

PROPHETIC EXAMPLE 8

The present example outlines the procedure contemplated by the Applicants to be useful for the successful imaging of surfaces to which prosthetic devices are to be fitted.

MRI of Amputated Human Long Limb Members

The limb to which a prosthetic device is to be fitted is prepared for attachment of a prosthetic device by surgical procedures as medically indicated to provide a suitable attachment surface. The surface is then coated with a material such as benzoin that will facilitate adherence of an applied powder to the surface. Zeolite-enclosed gadolinium, prepared as described in Example 1, is sufficiently to allow easy dispersion in a liquid or as an aerosol, washed extensively in water until the wash is free of gadolinium as determined by testing with xylenol orange, and then applied to the skin surface. Application is with an aerosol, either as a dry powder or as a suspension in a suspending agent such as alcohol or water. After the surface is coated with a fine layer of powder, images are obtained by standard magnetic imaging procedures. The resulting images are used to design custom matings for the artificial limb.

The present invention has been described in terms of particular embodiments found by the inventors to comprise preferred modes of practice of the invention. It will be appreciated by those of skill in the art that in light of the present disclosure numerous modifications and changes can be made in the particular embodiments exemplified without departing from the intended scope of the invention. For example, any of a number of zeolites or molecular sieves could be used as the enclosing matrix and any of a number of cationic species could be present within the zeolite, some of which could be used to modify effects of the enclosed ion of interest, for example, trivalent gadolinium in imaging studies. These and obvious related modifications are contemplated to be within the scope of the claims.

REFERENCES

The references listed below are incorporated herein by reference to the extent they supplement, explain, provide a background for or teach methodology, techniques and/or compositions employed herein.

Lönnemark, M., Hemmingsson, A., Bach-Gansmo, T., Ericsson, A., Öksendal, A. Nyman, R. and Moxnes, A., Acta Radiol. 30, 193–196 (1989).

Hahn, P. F., Staark, D. D., Lewis, J. M., Saini, S., Elizondo, G., Weissleder, R., Fretz, C. J. and Ferrucci, J. T., Radiology 175, 695–700 (1990).

Claussen, Von C., Kornmesser, W., Laniado, M., Kaminsky, S.,Hamm, B. and Felix, R., ROFO 148, 683–689 (1989).

Braybrook, H. H. and Hall, L. D., Drug. Des. Deliv. 4, 93–95 (1989).

Breck, D. W., Zeolite Molecular Sieves, Krieger Publishing Company, Malabar, Fla., 1984.

Rankel, L. A. and Valyocaik, E. W., U.S. Pat. No. 4,388,285, Jun. 14, 1983.

Messina, C. A., Lok, B. M. and Flanigen, E. M., U.S. Pat. No. 4,544,143 (1985).

Wilson, S. T. and Flanigen, E. M. U.S. Pat. No. 4,567,028 (1986).

I claim:

1. A magnetic resonance gastrointestinal tract imaging method comprising administering to a mammal an amount of molecular sieve-enclosed paramagnetic ion, said amount being effective as an image-brightening agent.

2. A magnetic resonance gastrointestinal tract imaging method comprising administering a framework-modified molecular sieve to a mammal in an amount effective an image-brightening agent wherein the framework is modified to include a paramagnetic ion.

3. The method of claim 1 or claim 2 wherein the paramagnetic ion comprises a rare earth or transition metal element.

4. The method of claim 1 or claim 2 wherein the paramagnetic ion comprises $V^{+4}$, $Cu^{+2}$, $V^{+3}$, $Ni^{+2}$, $Cr^{+3}$, $Co^{+2}$, $Fe^{+2}$, $Co^{+3}$, $Mn^{+2}$, $Gd^{+3}$, $Dy^{+3}$ or $Fe^{+3}$.

5. The method of claim 1 wherein the molecular sieve-enclosed paramagnetic ion comprises a free ion or a complexed ion.

6. The method of claim 5 wherein the complexed ion is formed from a multidentate ligand.

7. The method of claim 5 wherein the complexed ion comprises a nitroxide functional group.

8. The method of claim 1 wherein the molecular sieve is characterized as having ion exchange properties sufficient to facilitate preferential binding of the paramagnetic ion.

9. The method of claim 1 or claim 2 wherein the molecular sieve comprises faujasite (FAU), Linde type A (LTA) or ZSM-5 type (MFI) zeolite.

10. The method of claim 1 or claim 2 wherein the molecular sieve comprises mordenite (MOR) type zeolite.

11. The method of claim 1 wherein the molecular sieve is administered by direct injection into a fistulous region of the GI tract.

12. The method of claim 1 wherein the molecular sieve enclosed paramagnetic ion is administered orally.

13. A method for gastrointestinal tract bright imaging comprising administering a pharmaceutically acceptable molecular sieve-enclosed trivalent gadolinium formulation and detecting the gadolinium by magnetic resonance imaging.

14. The method of claim 13 wherein the molecular sieve-enclosed trivalent gadolinium is CaGdA or NaGdX.

15. The method of claim 13 wherein the trivalent gadolinium is chelated.

16. A method for gastrointestinal tract imaging comprising orally administering a pharmaceutically acceptable formulation comprising molecular sieve enclosed divalent manganese and detecting the manganese by magnetic resonance imaging.

17. The method of claim 16 wherein the molecular sieve-enclosed divalent manganese is CaMnA or NaMnX.

18. The method of claim 16 wherein the manganese is chelated.

19. A pharmaceutical composition for gastrointestinal tract imaging, said composition comprising an amount of a molecular sieve-enclosed paramagnetic ion in a pharmaceutically acceptable carrier effective to produce a bright image in vivo.

20. The pharmaceutical composition of claim 19 wherein the paramagnetic ion is chelated.

21. The pharmaceutical composition of claim 20 wherein chelation is with hydroxyquinoline, phthalic acid, or dipicolinic acid.

22. The pharmaceutical composition of claim 19 wherein the molecular sieve-enclosed paramagnetic ion is a transition metal ion.

23. The pharmaceutical composition of claim 19 wherein the paramagnetic ion comprises trivalent gadolinium.

24. The pharmaceutical composition of claim 19 wherein the paramagnetic ion comprises $Mn^{+2}$.

25. The pharmaceutical composition of claim 19 wherein the pharmaceutically acceptable carrier is a suspending liquid, powder, or absorbing matrix.

* * * * *

UNITED STATES PATENT AND TRADEMARK OFFICE
CERTIFICATE OF CORRECTION

PATENT NO. : 5,429,814
DATED : July 4, 1995
INVENTOR(S) : Stuart W. Young et al

It is certified that error appears in the above-indentified patent and that said Letters Patent is hereby corrected as shown below:

Title page the Notice should read —[*] Notice: The term of this patent shall not extend beyond the expiration date of Pat. No. 5,271,527.—

Signed and Sealed this

Twenty-eighth Day of November 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,429,814

DATED : Jul. 4, 1995

INVENTOR(S) : Stuart W. Young, et al

It is certified that error appears in the above-indentified patent and that said Letters Patent is hereby corrected as shown below:

Title page the Notice should read --[*] Notice: The term of this patent shall not extend beyond the expiration date of Pat. No. 5,122,363.--

This certificate supersedes Certificate of Correction issued November 28, 1995.

Signed and Sealed this

Fifteenth Day of October, 1996

Attest:

BRUCE LEHMAN

*Attesting Officer*  *Commissioner of Patents and Trademarks*